United States Patent [19]

Roberge et al.

[11] Patent Number: 4,891,186

[45] Date of Patent: Jan. 2, 1990

[54] REACTOR ANALYSIS SYSTEM

[75] Inventors: Raymond P. Roberge, Chappaqua; Arthur W. Francis, Jr., Monroe, both of N.Y.; Thomas G. Wolfe, Cos Cob, Conn.

[73] Assignee: Union Carbide Corporation, Danbury, Conn.

[21] Appl. No.: 193,196

[22] Filed: May 9, 1988

Related U.S. Application Data

[63] Continuation of Ser. No. 865,005, May 20, 1986, abandoned.

[51] Int. Cl.[4] .............................................. G01N 33/00
[52] U.S. Cl. ........................................ 422/83; 422/62; 436/55; 436/115; 436/124; 436/158
[58] Field of Search ...................... 422/62, 78, 70, 80, 422/81, 90; 436/103, 83, 115, 158, 55, 124

[56] References Cited

U.S. PATENT DOCUMENTS

| | | | |
|---|---|---|---|
| 3,026,184 | 3/1962 | Karosek | 427/62 |
| 3,304,159 | 2/1967 | Hinsvork | 436/115 |
| 3,961,896 | 6/1976 | Dunn | 422/90 |
| 4,106,908 | 8/1978 | Gryspeerdt | 436/158 |
| 4,121,922 | 10/1978 | Mackay et al. | 422/62 |
| 4,411,157 | 10/1983 | Babin et al. | 436/177 |

OTHER PUBLICATIONS

"Collaboration Results in New Way to Control Reactor Atmospheres", Tom Nelson, Vacuum Technology, Research and Development, Jan. 1986, pp. 79,80,82 and 83.

"Reactor Analysis System", Linde, Union Carbide-High Purity Gas Analysis Brochure printed 5/85, and First Published by Mailing to Interested Parties Subsequent to May 21, 1986.

*Primary Examiner*—Michael S. Marcus
*Attorney, Agent, or Firm*—Alvin H. Fritschler

[57] ABSTRACT

Gas samples withdrawn from within a reactor vessel, as well as from the feed gas thereto, are passed to gas analyzers for particular components or impurities desired to be measured. The response time of the reactor analysis system employed is advantageously minimized by the elimination of dead gas space upon the closing of control valves and the provisions for rapid purging of the system or of individual gas analyzer feed lines.

23 Claims, 1 Drawing Sheet

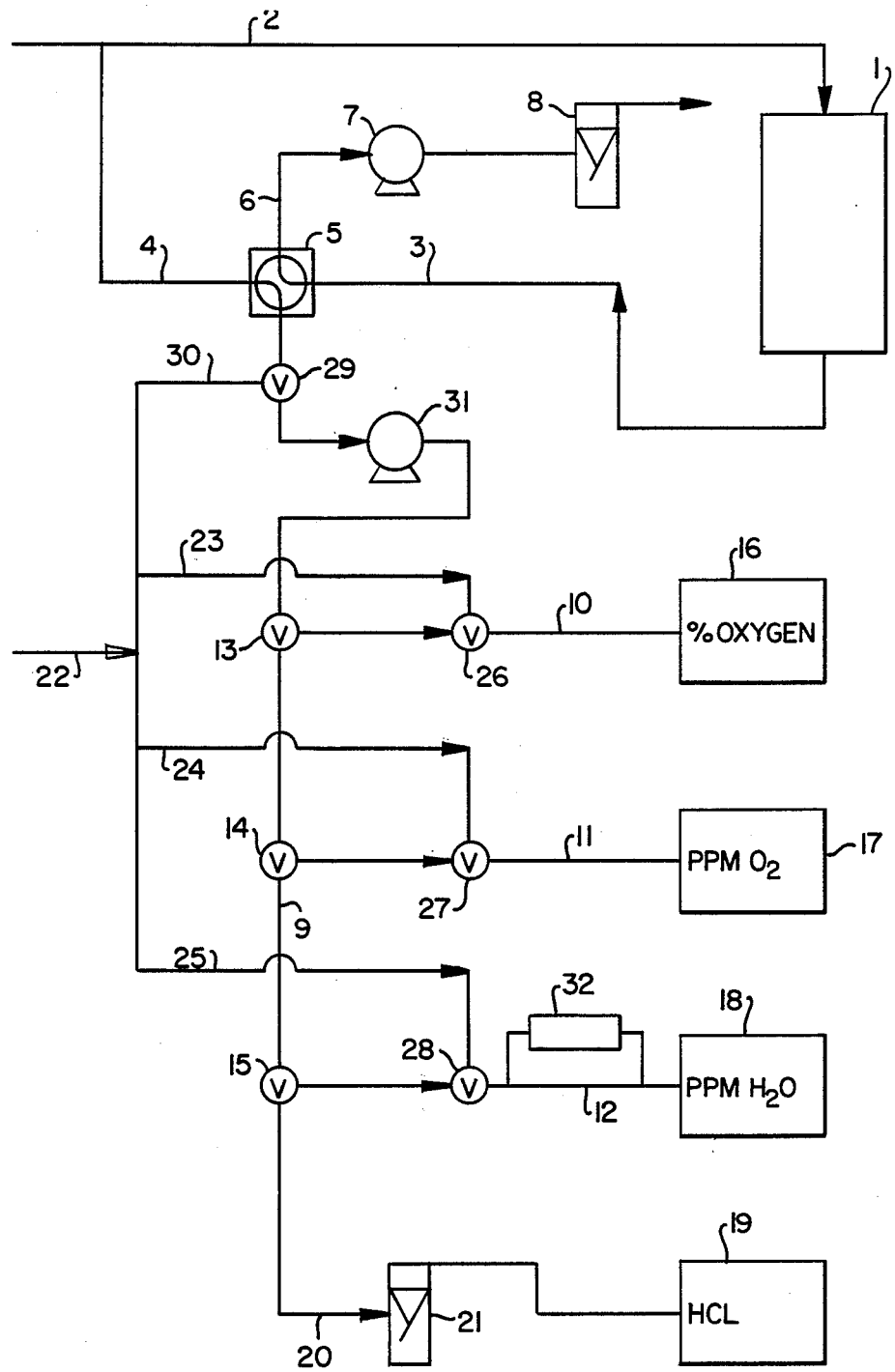

REACTOR ANALYSIS SYSTEM

This application is a continuation of prior U.S. application Ser. No. 865,005, filing date May 20, 1986, now abandoned.

BACKGROUND OF THE INVENTION

1. Field of the Invention -

This invention relates to the purity of gases. More particularly, it relates to the monitoring of the purity of gases within process reactors.

2. Description of the Prior Art

The purity of the gases employed in various processing operations, as in the semiconductor industry, often has a great effect on the product quality or the ultimate yield of product devices that are being produced. Considerable effort has been made in the art to develop analytical tools suitable for measuring the purity of process gases as received or generated at a manufacturing facility. However, little attention has been paid to the purity of such gases once they enter process equipment for use therein. Nevertheless, the ability to successfully monitor gas purity within a process reactor or other such equipment would be of appreciable benefit in the art, not only with respect to continuous on-line monitoring of processes requiring or benefiting by a critical control of gas purity, but also for the troubleshooting of processing problems, the establishing of baseline conditions with respect to new processing operations, and the developing of optimum processing conditions for enhancing product yields or achieving other desirable results.

There is a genuine need in the art, therefore, for the development of practical means for the monitoring of gas purity within processing equipment. Such means should desirably have relatively rapid response times, be capable of operation without the introduction of impurities into the processing operation being carried out, and be operable without affecting the flow rate through the processing system being analyzed. With the development of such means in convenient, readily operable form for practical commercial application, the numbers of processing activities that can benefit from such gas monitoring means is likely to increase as the potential benefits of such in situ analysis are appreciated with respect to such various processing activities.

It is an object of the invention, therefore, to provide a means for the monitoring of gases within a processing vessel.

It is another object of the invention to provide an analysis system capable of rapidly carrying out analyses with respect to gases withdrawn from within a processing vessel.

It is another object of the invention to provide a gas analysis system for the monitoring of gases from within a processing operation without interference with the performance characteristics thereof.

With these and other objects in mind, the invention is hereinafter described in detail, the novel features thereof being particularly pointed out in the appended claims.

SUMMARY OF THE INVENTION

Samples of gas from within a rector vessel, as well as feed gas to said vessel, can be analyzed for particular components, with the analysis system being adapted for rapid and thorough purging to minimize response time and to enhance the accuracy of the analyses obtained during continuous operation of the reaction being carried out in the reactor vessel. For such purposes, straight-through flow valves minimizing dead space upon the closing thereof are employed.

BRIEF DESCRIPTION OF THE DRAWING

The invention is further described herein with reference to the accompanying schematic drawing of an illustrative embodiment of the invention adapted for the monitoring of oxygen, moisture and HCl in the gas stream passed to a process reactor and as present within said reactor.

DETAILED DESCRIPTION OF THE INVENTION

The objects of the invention are accomplished by a novel combination of conduits, gas analyzers and control valves such as to enable gas samples to be analyzed, and the analyzers and associated conduits to be purged so as to minimize response time, wherein dead gas space within the system that could result in inaccurate analysis in the course of continuing gas monitoring activities is precluded. The invention not only enables the gas monitoring operations to be conveniently carried out without disruption of the process being monitored, but to be performed in a manner enabling the process to be analyzed, or fingerprinted in terms of the precise changes that may occur in the course of the process, in a manner not heretofore accomplished by practical, commercial analysis equipment.

With reference to the drawing, the process reactor vessel to be monitored is represented by the numeral 1, with feed gas passing to said reactor vessel through line 2. Conduit means 3 are provided for continually withdrawing representative gas samples from within reactor vessel 1 through a suitable exhaust gas manifold, and conduit means 4 are provided for continually withdrawing gas samples from the feed gas passing to said reactor vessel through line 2. Both gas samples are passed to valve means 5 adapted to continually receive said gas samples from lines 2 and 3 and to pass either one of said gas samples downstream thereof for analysis as described below. The gas sample that is not being analyzed at any given time is discharged from said valve means 5 is discharged from the system through discharge line 6 containing standby pump 7 and standby flowmeter 8 for convenient flow rate control purposes. Valve means 5 of conventional nature will be understood to be adjustable so as to pass the gas sample previously discharged from the system downstream for analysis, while discharging the gas sample previously being analyzed from the system as withdrawal of said gas samples is continued during any given gas analysis operation. Such continual withdrawal of gas from the feed gas stream to the reactor vessel and from within the reactor vessel itself assures against any undesired dislocation or variation of the conditions within the reactor vessel due to the carrying out of said gas monitoring operations.

A main gas supply flow line 9 is employed to pass the gas sample to be analyzed to individual gas analyzer feed lines, which in the illustrative embodiment are shown as lines 10, 11 and 12. In each of such individual feed lines, corresponding gas sample valve means 13, 14 and 15, respectively, are provided for tapping or drawing off individual samples of the gas to be analyzed from said main flow line 9. Said gas sample valve means, which can be added to or reduced depending upon the number of analyses desired with respect to any particular process operation being monitored, are generally adapted for straight-through flow of gas from main glow line 9. While gas is trapped within the connecting flow line upon the closing of such valve means, there is essentially no dead volume or gas space created thereby. Upon re-establishment of flow through said gas sample valve means, as by the passage of an inert gas therethrough between analysis, such trapped gas is readily flushed from the system. This feature is of critical importance to the minimizing of the response time of the system. In the absence of such form of gas sample valve means and upon the creation of dead gas space associated with the individual gas analyzer feed lines, it is found that the slow release or discharge of gas from such dead space will cause a variation in the gas analysis from the accurate reading desired at any given point in a processing operation. This unsatisfactory condition, avoided in the practice of the invention, would appreciably add to the required response time of the system, with accurate and precise readings during gas analysis not being obtainable until after the slow discharge of gas from said dead gas space has been completed.

The gas samples tapped from main flow line 9 through individual gas analyzer feed lines 10, 11 and 12 are passed to conventional gas analyzer means for separately analyzing the individual gas samples present in said feed lines, e.g. a percent oxygen analyzer 16, a parts per million (ppm) oxygen analyzer 17, and a moisture analyzer 18, respectively, in the illustrated embodiment.

The reactor analysis system of the invention is of major benefit in the fabrication of semiconductor devices, where the use of high-purity process gases are important to product yield, and the maintaining of such gas purity in the wafer processing environment is important to the achieving of optimum yield. In this application, the reactor vessel atmospheres are desirably sampled and measured for water moisture and oxygen contents as low as 0.1 ppm in inert gases, such as nitrogen, argon or helium, and for water as low as 0.1 ppm and hydrocarbons as low as 0.5 ppm in oxygen ambients. Because all three of such analyzers can be damaged by contact with HCl, its presence is desirably detected by a sensor that, upon determining that an undesirable amount of such HCl is present, allows or causes nitrogen or other inert purge gas to enter the system, as indicated above, while triggering an alarm that warns the system operator not to continue sampling gas. The sensors can be used also to determine whether a reaction vessel has been purged of all HCl used in cleaning operations. The system of the invention can also employ alarms to warn when water vapor levels approach the water analyzers limit, as well as other pertinent conditions, such as fan and fuse failures and the like. In the drawing, a conventional HCl analyzer 19 is supplied with gas from main flow line 9 through conduit line 20. Sample bypass flowmeter 21 is conveniently included in said line 20 to control the flow rate of sample gas through the system.

As indicated above, the minimizing of the system response time is an important aspect of the invention. Thus, it is desired to have inert purge gas readily available to rapidly purge the gas analyzer feed lines and the gas analyzers employed between analyses. Such purge enables gas analyses to be carried out rapidly during the course of the reaction accruing in the reaction vessel being monitored. For such purposes, purge gas supply means adapted to pass purge gas from a source of gas (not shown) to the gas analyzer feed lines for each individual gas sample to be analyzed are provided. In the drawing, such purge gas supply means is represented overall by the numeral 22, with separate purge gas supply conduits 23, 24 and 25 being used to pass purge gas to gas analyzer feed lines 10, 11 and 12, respectively. Control means are provided in each of said gas analyzer feed lines for selecting either the individual samples of the gas to be analyzed or said purge gas as the gas to be passed to said gas analyzer means. Such control means, of conventional design, are shown as control valves 26, 27 and 28 in said gas analyzer feed lines 10, 11 and 12, respectively.

The purge gas supply to the system also desirably includes purge control means 29 adapted to enable either the gas sample to be analyzed, or said purge gas available from supply means 22 through line 30, to be passed through said main gas supply flow line 9 for analysis. It will be appreciated that, where such purge control means 29 are employed, it is possible to purge the entire gas analysis system or, alternatively, to pass purge gas directly to one or more of said individual gas analyzer feed lines, while a gas sample to be analyzed is passed through main flow line 9 for analysis in particular analyzers other than these being purged. With respect to any gas trapped in the individual feed lines upon closing of said gas sample valve means, but without being positioned in any gas dead space, it will be appreciated that the straight-through flow of gas, e.g. nitrogen or other inert purge gas, will rapidly flush such gas from the system to facilitate the desired rapid response time of the system.

It will be appreciated that various changes or modifications can be made in the details of the invention as herein described without departing from the scope thereof as set forth in the append claims. While it is highly desirable to withdraw gas samples both from within the reactor vessel and from the feed gas entering the reactor vessel, it will be appreciated that, if desired, gas samples from within the reactor vessel can be analyzed without the requirement for also analyzing said feed gas. While the reactor analysis system of the invention can be employed in the form disclosed above and illustrated in the drawing, with only said gas sample from within the reactor vessel being analyzed, it is also possible to modify the system so as to provide only for the withdrawal of a gas sample from within the reactor vessel. In such an alternative, it will be appreciated that a main gas supply line, sample means, individual gas analyzer feed lines and desired gas analyzers would be employed, as in the illustrated embodiment. Similarly, the purge gas supply means and the control means for selecting either individual gas samples or said purge gas for passage through the gas analyzers would be as described above. Means would likewise be desirably provided to enable purge gas to pass through the main gas supply flow line and, in appropriate cases, such as described above, to provide a HCl or other necessary analyzer to avoid the passage of a gas to the other analyzers that would be harmful to such analyzers.

The various control valves employed in the practice of the invention are all standard, commercially available items of equipment that can readily be employed to achieve the novel combination of elements that comprises the subject reactor analysis system. Valve means 5, as employed in the desired practice wherein samples of gas are continually withdrawn from within the reactor vessel and from the feed line thereto, is conveniently a well known four way ball valve, such as a Whitey four way valve that allows a constant flow of gas samples simultaneously through both of its sample or inlet ports, one such sample being passed to said main gas flow line 9, while the other is being diverted through discharge line 6. Control valves 26, 27 and 28 can also be any suitable, commercially available valve adapted to select either the gas sample to be analyzed or purge gas for passage therethrough to the corresponding gas analyzers. A three way bellows valve marketed by Nupro Company of Willoughby, Ohio is conveniently employed for such control valve purposes. Similarly, a three port bellows valve is an example of a suitable, commercially available valve means for the tapping of samples from main flow line 9 for passage through individual gas analyzer feed lines, such as said feed lines 10, 11 and 12. Such three port bellows valves allow a modular approach to manifolding without costly machining of manifold blocks. Any number of individual valves may be added at any time. Such three port bellows valves, marketed by Nupro Company, have straight-through flow paths that allow uninterrupted flow, with said ports used for the withdrawal of samples, as described in the present application, or for injection purposes. The bellows seal in such valves is out of the flow path when the valve is closed, minimizing dead space and interruption of flow. Such valves, by the use of packless bellows seals, eliminate the need for the valve lubrication normally associated with O-Ring seals and gaskets, thereby eliminating contamination thereby in systems, such as that of the invention, in which high purity is either necessary or highly desired.

Standard gas analyzers will be employed for any desired gas component or impurity concentration desired to be measured and monitored. For the semiconductor application referred to above, conventional oxygen, water (moisture), and HCl analyzers are readily available in the art, with the percent oxygen analyzer conveniently being used to measure oxygen concentrations of about 0.01 to 100%, and the ppm oxygen analyzer being used to measure ppm concentrations of oxygen. The particular levels of concentration measured can, of course, be varied in accordance with the requirements of a given application and the capabilities of the analyzers employed. In general, the percent oxygen analyzer is of faster operation than the ppm analyzer, and is commonly used to detect a rapid increase in oxygen concentration, as by the passage of air into the reactor vessel, so that the ppm oxygen analyzer can be shut down before undesirable exposure thereof to very high concentrations of oxygen beyond its design capability. A suitable, commercially available percent oxygen analyzer is a high temperature zirconia sensor marketed by Sybron. Zirconiz cells, which can measure oxygen contents of from about 1 ppm to 100%, develop a voltage proportional to the oxygen concentration is the sample. The cell is temperature controlled, and is capable of providing accurate results over a wide range of sample flow rates when used in inert or oxygen atmospheres. Trace or ppm oxygen analyzers are also readily available in commerce, with a Teledyne instrument being suitable for purposes of the invention. Its sensor is an electrochemical transducer that is specific to oxygen. The transducer use an aqueous electrolyte, with a water bubbler column desirably used to humidify the sample entering the analyzer and avoid drying out of the electrolyte and deactivation of the sensor. The sample gas stream passes over the electrolyte-covered cathode, initiating an electrochemical reaction. The flow of current between the cathode and anode is directly proportional to the oxygen concentration in the sample stream. As suggested above, the system is advantageously employed with the control means in the Gas Analyzer Feed Lines being adapted to pass purge gas to the parts per million oxygen analyzer when the oxygen content of the individual gas samples exceed a predetermined, acceptable level, and to pass gas samples thereto when said oxygen content is below said predetermined level. For moisture analysis, a ppm moisture analyzer marketed by DuPont is conveniently employed in the practice of the invention. This analyzer is a microprocessor-controlled instrument that can measure trace concentrations of water vapor in liquid-free gases, measured in ppm. The sensor of this instrument is a piezoelectric crystal coated with a thin film of moisture-absorptive material. The coating absorbs moisture from the sample gas stream and, depending on the resulting mass of the coating, alters the frequency of the current created by the crystal. Every 30 seconds, the sample and a dry reference gas stream are switched so that they alternately flow through, or bypass, the sensor cell. The cell is thereby alternately moistened and then dried by the sample and reference gases. The resulting altered frequency is proportional to the moisture content of the sample stream.

As indicated above, a sensitive monitor is desirably provided in the illustrative embodiment to protect the oxygen and moisture instruments from attack by hydrogen chloride. A Sensidyne HCl monitor is an example of a suitable, commercially available instrument for this purpose. It has a diffusion-type electrochemical gas detector that selectively responds to HCl. Hydrogen chloride molecules in the gas stream will permeate the external membrane and react with an internal electrolyte that surrounds the sensor electrode. This chemical reaction generates an electrical current proportional to the steady state flux of HCl permeating the membrane. An electronics module measures the electrochemically generated current and converts it to a 4–20 milliamp signal. For purposes of the invention, all gas analyzers are automatically switched to an inert nitrogen purge phase in the event HCl concentrations of 10 ppm or more are sensed by said HCl sensitive monitor.

In the practice of the invention, it will be understood that a sample pump 31 is provided for the pumping of the appropriate gas stream through main gas supply flow line 9 at a desired flow rate. Any suitable, commercially available gas pump, such as a stainless steel bellows pump, can be used for this purpose. It is also within the scope of the invention to provide a conventional catalytic oxidizer unit, generally represented by the numeral 32, for use in conjunction with individual gas analyzer feed line 12 for moisture monitoring as is shown in the drawing. As will be readily understood by those skilled in the art, the catalyst bed of such an oxydizer unit enables the total hydrocarbons in oxygen to be measured by the conversion of such hydrocarbons to water and carbon dioxide, with measurement of the resulting increase in water concentration by means of moisture analyzer 18. This feature enables hydrocarbons to be measured without the need for fuel, zero or span gases that are required for the separate, traditional measurement of hydrocarbons, i.e., by use of a flame ionization detector.

Those skilled in the art will appreciate that the reactor analysis system of the invention will be employed in a manner, and with specific operating conditions and analysis capability, dependent upon the processing operation being monitored and the particular component or impurity concentrations desired to be analyzed. The flow rates through the system will vary depending upon the particular application thereof, but, for the semiconductor application referred to above, gas flow rates of from about 0.5 to about 5 liters per minute through main flow line 9 have been found convenient, with a flow rate of about 0.6 liters per minute being generally preferred to such application in which the indicated oxygen, moisture and HCl monitoring is carried out. The system can also be used to measure the desired components or impurities at any convenient pressure, with oxygen and water in inert gas being conveniently measured at pressures on the order of from atmospheric pressure to 100 psi. It will also be understood that any suitable purge gas can be employed in the operation of the system. While nitrogen is a generally preferred purge gas, argon, helium or other gases can also be employed.

As indicated above, the invention can be used to great advantage for the monitoring of gas impurities in semiconductor manufacturing processes. In various operations involving batch type cyclic processing sequences, commonly with variations such as heating and cooling within the reaction vessel, or portions thereof, it is necessary to minimize response time, as in the system of the invention, in order to monitor conditions within the reaction vessel in a meaningful manner. Some systems that could be developed for the desired gas monitoring purposes might require as much as 20 minutes to provide accurate and precise readings, due to dead gas space conditions and the like as discussed above. By contrast, the system of the invention can be used to obtain accurate and precise monitoring of gases from within a reactor vessel, as well as of feed gases to such a vessel, in less than five minutes, even in as little time as about one minute. This is particularly important in applications wherein the atmospheres are varying during the course of the operation being monitored, as by passage from an oxygen atmosphere to a nitrogen atmosphere and back for particular semiconductor production operations.

The creation of gate oxides on partially processed silicon wafers by heating such wafers in a quartz furnace in a pure oxygen atmosphere to form this layers of silicon dioxide, followed by annealing of the wafer in an inert atmosphere at high temperature to reduce the fixed oxide charge is an operation in which the reactor analysis system of the invention can be employed to great advantage. The high level of sensitivity and speed obtainable in the system of the invention make it possible to detect gas impurity levels that would interfere with the desired semiconductor production operation. Even a small amount of impurity in a reactor, i.e. furnace, atmosphere might raise the threshold voltage needed to activate a semiconductor component to the point where it cannot be activated. The invention enables the furnace to be analyzed in terms of the actual atmosphere in which the processing operations are carried out, thus enabling such operations to be diagnosed in a meaningful manner so that various processing atmosphere problems can be quickly identified and corrected. The invention can be conveniently used for such diagnostic and furnace qualify purposes, and for related troubleshooting, on-line gas purity monitoring, process development and the like, performing a valuable function not previously available in the art. By the essential elimination of all dead gas space from the system, and the provisions for enabling each analyzer to be purged independently of others in the system as described above, the response time of the system is desirably minimized. Such features of the invention are extremely important for in-situ monitoring in cyclic processes in which the total cycle time for a sequential series of operations is on the order of one hour or less. The reactor analysis system of the invention will thus be seen to represent a highly significant and versatile advance in the art, enabling monitoring, diagnostic, troubleshooting, testing and development operations to be carried out with respect to the conditions within reactor vessels in a manner not previously available in the art.

We claim:

1. An analysis system for monitoring a feed gas stream passing to and a gas present within a process reactor comprising:
   (a) conduit means for continually withdrawing samples of a gas present within a reactor;
   (b) conduit means for continually withdrawing samples from a feed gas stream passing to the reactor;
   (c) a first valve means continually receiving samples from said conduit means containing samples of the gas present within the reactor and from said conduit means containing samples of the feed gas passing to the reactor, wherein said first valve means in a first position passes the sample of the gas present within the reactor downstream for analysis while discharging the sample of the feed gas from the system, and wherein said first valve means in a second position passes the sample of the feed gas stream downstream for analysis while discharging the sample of the gas present within the reactor;
   (d) a main gas supply flow line for passing the gas sample to be analyzed from said first valve means to individual gas analyzer feedlines;
   (e) a second gas sample valve means for tapping one or more individual samples of the gas sample to be analyzed from the main flow line, said second valve means being adapted for continuous straight through flow of the gas sample from said main flow line, said second valve means also being adapted to periodically tap the individual sample to be analyzed from said main flow line, with essentially no dead volume being created upon closing of said periodic tap means of said second valve means to discontinue the tapping of the gas sample for analysis;
   (f) gas analyzer feed lines for withdrawing the individual gas samples from said second sample valve means for analysis;
   (g) gas analyzer means for separately analyzing the individual gas samples present in said gas analyzer feed lines for a particular gas stream component;
   (h) purge gas supply means adapted to pass purge gas to said gas analyzer feed lines for each individual gas sample for analysis; and
   (i) control means in said gas analyzer feed lines for selecting either the individual samples of the gas to be analyzed or the purge gas to be passed to said gas analyzer means, whereby said system enables gas samples from the feed gas passing to the reactor and samples taken from the gas present within the reactor to be accurately monitored with rapid response time, the purge gas being available to rapidly and essentially completely purge said gas analyzer feed lines and said gas analyzer means between analyses, thus enabling accurate gas analysis to be carried out rapidly during the course of operation.

2. The analysis system of claim 1 and including purge control means adapted to enable either the gas sample to be analyzed or the purge gas to be passed through said main gas supply flow line.

3. The analysis system of claim 1 and including pump means for withdrawing the gas sample being discharged from said system after passage (to) through said first valve means (c).

4. The reactor analysis system of claim 1 in which said valve means (c) comprises a four way valve ball valve adapted for the constant flow of gas through two sample ports simultaneously.

5. The analysis system of claim 1 in which said gas analyzer means comprises means for separately analyzing an individual gas sample for oxygen and moisture.

6. The analysis system of claim 5 in which separate gas analyzer means are provided for measuring percent oxygen concentrations of from about 0.01 to 100% and for measuring parts per million oxygen, said control means being adapted to pass purge gas to said parts per million analyzer when the oxygen content of the gas sample to be analyzed exceeds a predetermined level, and to pass said individual gas sample from the gas sample to be analyzed thereto when the oxygen content is below said predetermined level.

7. The analysis system of claim 6 and including a catalytic oxidizer unit optionally operable in said gas analyzer feed line to said moisture analyzer, said unit being suitable for the conversion of hydrocarbons in oxygen to water and carbon dioxide, the increase in water concentration in said moisture analyzer constituting a measurement of the total concentration of hydrocarbons in the gas sample being analyzed.

8. The analysis system of claim 5 and including means for analyzing the gas sample from said main flow line for the presence of HCl, and conduit means for supplying the gas sample in said main flow line to said HCl analysis means.

9. The analysis system of claim 8 and including sample by-pass means in said conduit means for supplying gas from said main flow line to said HCl analysis means.

10. The analysis system of claim 8 in which separate gas analyzer means are provided for measuring percent oxygen concentrations of from about 0.01 to 100% and for measuring parts per million oxygen, said control means being adapted to pass purge gas to said parts per million analyzer when the oxygen content of the gas sample to be analyzed exceeds a predetermined level, and to pass the gas sample thereto when said oxygen content is below the predetermined level.

11. The analysis system of claim 8 and including control means for switching from said individual gas sample to said purge gas in at least on of said individual gas analyzer feed lines if said HCl concentration is 10 ppm or greater.

12. The analysis system of claim 1 wherein said control means (i) for selecting either the gas sample or the purge gas to be passed to said analyzer comprises a third valve means placed in a line through which the gas sample passes on its way to said gas analyzer, whereby essentially no dead volume is created between said purge gas supply means and said gas sample feed line.

13. The analysis system of claim 1 and including pump means for the pumping of the gas sample to be analyzed through said main flow line.

14. The analysis system of claim 13 and including a forth valve means positioned between said first valve means and said pump means, said forth valve means comprising a control means for selecting either said gas sample to be analyzed or said purge gas to be passed to said main flow line.

15. An analysis system for monitoring a gas stream within a process comprising:
  (a) conduit means for continually withdrawing gas samples from within said process;
  (b) a main gas supply line for passing a gas sample to be analyzed to individual gas analyzer feed means:
  (c) sample valve means for tapping one or more individual samples of the gas to be analyzed from said main flow line, said valve means being adapted for continuous straight-through flow of gas from said main flow line, said valve means also being adapted to periodically tap said individual sample to be analyzed from said main flow line, with essentially no dead volume being created upon closing of said valve means to discontinue the tapping of the gas sample for analysis;
  (d) gas analyzer feed means for withdrawing individual gas samples from said sample valve means for analysis;
  (e) gas analyzer means for separately analyzing the individual gas samples from said gas analyzer feed means for a particular gas stream component;
  (f) purge gas supply means adapted to pass purge gas to each individual gas analyzer feed means;
  (g) control means in said gas analyzer feed means for selecting either the individual gas samples of the gas to be analyzed or the purge gas to be passed to said gas analyzer means, whereby said system enables gas samples taken from within the process to be accurately monitored with a rapid response time, the purge gas being available to rapidly purge said gas analyzer feed means and said gas analyzer means between analyses, thus enabling accurate gas analysis to be carried out rapidly during the course of operation.

16. The analysis system of claim 15 and including purge control means adapted to enable either said gas sample to be analyzed or said purge gas to be passed through said main gas supply flow line.

17. The analysis system of claim 15 wherein said control means (g) for selecting either gas sample or purge gas to be passed to said analyzer comprises a second valve means placed in a line through which said gas sample passes on its way to said gas analyzer, whereby essentially no dead volume is created between said purge gas supply means and said sample feed line.

18. The analysis system of claim 15 in which said gas analyzer means comprises means for separately analyzing said individual gas samples for oxygen and moisture.

19. The analysis system of claim 18 in which separate gas analyzer means are provided for measuring percent oxygen concentrations of from about 0.01 to 100% and or measuring parts per million oxygen, said control means being adapted to pass purge gas to said parts per million analyzer when the oxygen content of said gas to be analyzed exceeds a predetermined level, and to pass individual gas sample from said gas to be analyzed thereto when said oxygen content is below said predetermined level.

20. The analysis system of claim 18 and including means for analyzing said gas sample from said main flow line for the presence of HCl, and conduit means for supplying gas in said main flow line to said HCl analysis means.

21. The analysis system of claim 20 in which separate gas analysis means are provided for measuring percent oxygen concentrations of from about 0.01 to 100%, and for measuring parts per million oxygen, said control means being adapted to pass purge gas to said parts per million analyzer when the oxygen content of said gas to be analyzed exceeds a predetermined level, and to pass individual gas sample from said gas to be analyzed thereto when said oxygen content is below said predetermined level.

22. The analysis system of claim 20 and including sample by-pass means in said conduit means for supplying gas from said main flow lines to said HCl analysis means.

23. The analysis system of claim 20 and including control means for switching from said individual sample of said gas to be analyzed to said purge gas in at least one of said gas analyzer feed means if said HCl concentration is 10 ppm or greater.

* * * * *